United States Patent
Kramer et al.

(10) Patent No.: US 8,048,921 B2
(45) Date of Patent: Nov. 1, 2011

(54) AMINO ACID COMPOUNDS

(76) Inventors: Ronald Kramer, Phoenix, AZ (US); Alexander Nikolaidis, New Kallikratia (GR)

( * ) Notice: Subject to any disclaimer, the term of this patent is extended or adjusted under 35 U.S.C. 154(b) by 400 days.

(21) Appl. No.: 12/337,012

(22) Filed: Dec. 17, 2008

(65) Prior Publication Data

US 2009/0137670 A1 May 28, 2009

Related U.S. Application Data

(63) Continuation-in-part of application No. 11/950,273, filed on Dec. 4, 2007, now Pat. No. 7,777,074.

(60) Provisional application No. 60/973,229, filed on Sep. 18, 2007.

(51) Int. Cl.
*A61K 31/205* (2006.01)
*C07C 229/00* (2006.01)

(52) U.S. Cl. ..................... 514/556; 562/567

(58) Field of Classification Search .......... 514/556; 562/567

See application file for complete search history.

(56) References Cited

U.S. PATENT DOCUMENTS 4,379,177 A 4/1983 McCoy et al.
4,743,614 A 5/1988 Terano et al.

OTHER PUBLICATIONS

Xu et al., 2005, CAS: 143:103285.*
Jablecka et al., Med Sci Monit 10(1):CR29-32 (2004).
Maynard et al., J. Nutr. 131:287-290 (2001).
Rytlewski et al., European Journal of Obstetrics & Gynecology and Reproductive Biology 138:23-28 (2008).
Schwedheim et al., Br J Clin Pharmacol 65(1):51-59 (2007).
Smith et al., J. Thorac Cardiovasc. Surg 132:58-65 (2006).
Rytlewski et al., Eur J. Clin Invest 35 (1):32-37 (2005).
Ming et al., Circulation 110:3708-3714 (2004).
Romero et al., Cardiovascular Drug Reviews 24(3-4):275-290 (2006).
Oka et al., Vasc Med 10:265-274 (2005).
Hayashi et al., PNAS 102(38):13681-13686 (2005).
Grasemann et al., Eur Respir J 25:62-68 (2005).
Boger, J. Nutr 137:1650S-1655S (2007).
Beghetti et al., J. Thorac Cardiovasc. Surg 132(6):1501-1502 (2006).
Larsen et al., B. Acta Physiol 191(1):59-66 (2007).
Berge, Journal of Pharmaceutical Sciences, Jan. 1977, vol. 66, No. 1.
Takahashi et al., "Characterization of the influence of nitric oxide donors on intestinal absorption of macromolecules," International Journal of Pharmaceutics vol. 286:89-97 (2004).
Fetih et al., "Nitric oxide donors can enhance the intestinal transport and absorption of insulin and [Asu 1,7]-eel calcitonin in rats," Journal of Controlled Release vol. 106:287-297 (2005).
Fetih et al., "Excellent Absorption Enhancing Characteristics of NO Donors for Improving the Intestinal Absorption of Poorly Absorbable Compound Compared with Conventional Absorption Enhancers," Drug Metab. Pharmacokinet. vol. 21(3):222-229 (2006).
Aniya et al., "Evaluation of Nitric Oxide Formation from Nitrates in Pig Coronary Arteries," Jpn. J. Pharmacal. vol. 71: 101-107 (1996).
T.F. Luscher, "Endogenous and exogenous nitrates and their role in myocardial ischaemia," Br. J. Clin. Pharmacol. vol. 34:29S-35S (1992).
Shiraki et al., "The hypotensive mechanisms of the new anti-anginal drug, N-(2-Hydroxyethyl) Nicotinamide Nitrate (Sg-75) in beagle dogs," Japan. J. Pharmacol. vol. 31:921-929 (1981).
CFIndustries, "Material Safety Data Sheet for Urea Ammonium Nitrate Solution (UAN)," available at www.cfindustries.com/pdf/UANMSDS.pdf Oct. 25, 2006.
Slart et al., "Nitrate Administration Increases Blood Flow in Dysfunctional but Viable Myocardium, Leading to Improved Assessment of Myocardial Viability: A Pet Study," J. Nucl. Med. vol. 47: 1307-1311 (2006).
Fayers et al., "Nitrate tolerance and the links with endothelial dysfunction and oxidative stress," Blackwell Publishing Ltd Br. J. Clin. Pharmacol. vol. 56:620-628 (2003).
Harm J. Knot. "Nitrate Tolerance in Hypertension New Insight Into a Century-Old Problem," Circulation Research vol. 93:799-801 (2003).
Schulz et al., "Functional and Biochemical Analysis of Endothelial (Dys)function and NO/cGMP Signaling in Human Blood Vessels With and Without Nitroglycerin Pretreatment," Circulation Research vol. 105:1170-1175 (2002).
Hatanaka et al., "Stereoselective Pharmacokinetics and Pharmacodynamics of Organic Nitrates in Rats," J Pharmacol Exp Ther. vol. 298(1):346-53 (2001).
"Glyceryl trinitrate—leaflet print—Patient UK," available at http://www.patient.co.uk/printer.asp?doc=30003883.
Chabot et al., "Characterization of the vasodilator properties of peroxynitrite on rat pulmonary artery: role of poly (adenosine 5'-diphosphoribose) synthase," British Journal of Pharmacology vol. 121:485-490 (1997).
Bauer et al., "Vascular and Hemodynamic Differences between Organic Nitrates and Nitrites," The Journal of Pharmacology and Experimental Therapeutics JPET vol. 280:326-331 (1997).
Niu et al., Eur J. Pharmacol 580:169-174 (2008).
Tan et al., Vasc Pharmacol 46:338-345 (2007).
Ahtee et al., J. Nutr 116:2555-2556 (1986).
Bloomer et al., J Int Soc Sports Nutr 4(22):1-6 (2007).
Ramaswamy et al., J. Raman Spectrosc. 34:50-56 (2003).
Rajkumar and Ramakrishnan, J. Raman Spectrosc. 31:1107-1112 (2000).
Petrosyan et at, J. Molecular Structure 794:160-167 (2006).

\* cited by examiner

*Primary Examiner* — Rei-tsang Shiao
(74) *Attorney, Agent, or Firm* — Booth Udall, PLC

(57) ABSTRACT

Carnitine and Taurine Compounds are described. The Carnitine Compound comprises Carnitine and one of a Nitrate and a Nitrite. The Taurine Compound comprises Taurine and one of a Nitrate and a Nitrite.

6 Claims, No Drawings

AMINO ACID COMPOUNDS

CROSS REFERENCE TO RELATED APPLICATIONS

This application is a continuation-in-part application of the earlier U.S. Utility patent application to Ronald Kramer, et. al. entitled "Amino Acid Compounds," application Ser. No. 11/950,273, filed Dec. 4, 2007, now pending, which application claims the benefit of the filing date of U.S. Provisional Patent Application 60/973,229 entitled "Amino Acid Compounds" to Alexander Nikolaidis and Ronald Kramer which was filed on Sep. 18, 2007, the disclosures of which is hereby incorporated entirely herein by reference.

BACKGROUND

1. Technical Field

Aspects of this document relate generally to Taurine and Carnitine Compounds.

2. Background

It is desirable to design new Taurine and Carnitine compounds that have properties lacking in conventional Taurine and Carnitine compounds, conventional Nitrate compounds, conventional Nitrite compounds, and in single-administration Taurine and Carnitine products.

SUMMARY

In one aspect, this document features a carnitine compound comprising Carnitine and one of a Nitrate and a Nitrite.

Particular embodiments may include one or more of the following. The Carnitine compound may further comprise a pharmaceutically acceptable additive, wherein the additive is one of a carrier, excipient, binder, colorant, flavoring agent, preservative, buffer, diluent, and combinations thereof. The Carnitine compound may be in the form of a capsule, tablet, pill, liquid, liquid suspension, vapor, gas, powder, granulate or pulverulence.

In another aspect, this document features a carnitine compound comprising Taurine and one of a Nitrate and a Nitrite.

Particular embodiments may include one or more of the following. The Taurine compound may further comprise a pharmaceutically acceptable additive, wherein the additive is one of a carrier, excipient, binder, colorant, flavoring agent, preservative, buffer, diluent, and combinations thereof. The Taurine compound may be in the form of a capsule, tablet, pill, liquid, liquid suspension, vapor, gas, powder, granulate or pulverulence.

In yet another aspect, this document features a method for increasing water solubility of one of Carnitine and Taurine in a human or animal, which comprises administering a pharmaceutically effective amount of one of a Carnitine Compound comprising Carnitine and one of a Nitrate and a Nitrite and a Taurine Compound comprising Taurine and one of a Nitrate and a Nitrite to the human or animal.

Particular embodiments may include one or more of the following. Increasing water solubility may further comprise increasing the bioabsorption of one of Carnitine and Taurine in a human or animal. Increasing water solubility may further comprise increasing the vasodilative characteristics of one of Carnitine and Taurine in a human or animal.

In still another aspect, this document features a method for preventing the development of nitrate tolerances in a human or animal, which comprises administering a pharmaceutically effective amount of one of a Carnitine Compound comprising Carnitine and one of a Nitrate and a Nitrite and a Taurine Compound comprising Taurine and one of a Nitrate and a Nitrite to the human or animal.

The foregoing and other aspects, features, and advantages will be apparent to those of ordinary skill in the art from the DESCRIPTION and from the CLAIMS.

DESCRIPTION

Overview

Compounds containing both a carboxyl group and an amino group are typically known as Amino Acids. Amino Acids typically have the basic formula X—R, wherein X is:

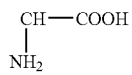

Amino Acids typically differ from one another with respect to the structure of the R group. It is the structure of the R group that typically determines the individuality and character of each Amino Acid.

In addition, many Amino Acid derivatives and products of Amino Acid biosynthesis themselves may have biological and physiological effects.

For example, Carnitine is a quaternary ammonium compound biosynthesized from the amino acids lysine and methionine. Acetyl-L-Carnitine is an alternative form of carnitine with an acetyl group coupled with the hydroxyl group of the third carbon molecule. Propionyl-L-carnitine is another alternative form of carnitine that contains a propionyl group coupled with the third carbon molecule. The chemical structures of Carnitine, Acetyl-L-Carnitine, and Propionyl-L-carnitine are as follows:

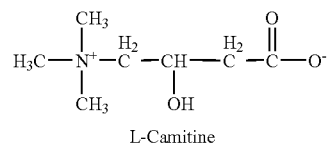

L-Carnitine

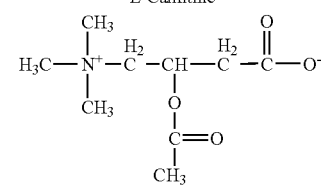

Acetyl-L-Carnitine

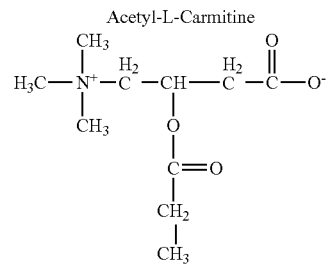

Propionyl-L-Carnitine

Significantly, neither carnitine nor its alternative forms possess vasodilating properties. In addition, since carnitine and its alternative forms are bipolar molecules, their solubility might be lowered with respect to pH. Carnitine is presently used in the dietary supplement industry to supplement Carnitine production in the body. Carnitine is also presently used in the dietary supplement industry to improve athletic performance, enhance mood, and boost immune response. Various supplemental Carnitine forms are available in the consumer marketplace.

In addition to the foregoing example, Taurine is a derivative of the sulfur-containing amino acid Cysteine. Taurine by itself has no vasodilating properties. Taurine is presently used in the dietary supplement industry to supplement Taurine production in the body. Taurine is also presently used in the dietary supplement industry to improve athletic performance and resist muscle cramps. Various supplemental Taurine forms are available in the consumer marketplace, including many sports supplements and energy drinks.

Nitrates are a class of compounds that are salts of Nitric Acid ($HNO_3$) and at least comprise one Nitrogen atoms and three Oxygen atoms ($NO_3$). In addition, Nitrites are a class of compounds that are salts of Nitrous Acid ($HNO_2$) and at least comprise one Nitrogen atom and two Oxygen atoms ($NO_2$).

Nitrates and Nitrites are commercially available in various preparations and are used in various commercial applications. In the case of ingestion by humans, Nitrate ($NO_3$) is typically reduced to Nitrite ($NO_2$) in the epithelial cells of blood vessels. In vivo, Nitrite ($NO_2$) reacts with a thiol donor, principally glutathione, to yield Nitric Oxide (NO).

TERMINOLOGY AND DEFINITIONS

In describing implementations of an Amino Acid Compound, the following terminology will be used in accordance with the definitions and explanations set out below. Notwithstanding, other terminology, definitions, and explanations may be found throughout this document, as well.

As used herein, "Amino Acid" is a term used in its broadest sense and may refer to an Amino Acid in its many different chemical forms including a single administration Amino Acid, its physiologically active salts or esters, its combinations with its various salts, its tautomeric, polymeric and/or isomeric forms, its analog forms, its derivative forms, its biosynthesis products and/or its decarboxylation products. Amino Acids comprise, by way of non-limiting example: Agmatine, Beta Alanine, Arginine, Asparagine, Aspartic Acid, Cysteine, Glutamine, Glutamic Acid, Glycine, Histidine, Isoleucine, Leucine, Lysine, Methionine, PhenylBeta Alanine, Proline, Serine, Threonine, Tryptophan, Tyrosine, and Valine.

As used herein, "Compound" is a term used in its broadest sense and may refer to an Amino Acid in combination with one of a Nitrate and a Nitrite.

As used herein, "Nitrate" is a term used in its broadest sense and may refer to an Nitrate in its many different chemical forms including a salt of Nitric Acid, a single administration Nitrate, its physiologically active salts or esters, its combinations with its various salts, its tautomeric, polymeric and/or isomeric forms, its analog forms, and/or its derivative forms. Nitrate comprises, by way of non-limiting example, many different chemical forms including dinitrate and trinitrate. Nitrates may be salts, or mixed salts, of Nitric Acid and comprise one Nitrogen atom and three Oxygen atoms. For the exemplary purposes of this disclosure, Nitrate may comprise salts of Nitrate such as sodium nitrate, potassium nitrate, barium nitrate, calcium nitrate, and the like. For the exemplary purposes of this disclosure, Nitrate may include mixed salts of Nitrate such as nitrate orotate, and the like. Additionally, for the exemplary purposes of this disclosure, Nitrate may comprise nitrate esters such as nitroglycerine, and the like.

As used herein, "Nitrite" is a term used in its broadest sense and may refer to an Nitrite in its many different chemical forms including a salt of Nitrous Acid, a single administration Nitrite, its physiologically active salts or esters, its combinations with its various salts, its tautomeric, polymeric and/or isomeric forms, its analog forms, and its derivative forms. Nitrite comprises, by way of non-limiting example, many different chemical forms including dinitrite and trinitrite. Nitrites may be salts, or mixed salts, of Nitrous Acid and comprise one Nitrogen atom and two Oxygen atoms. For the exemplary purposes of this disclosure, Nitrite may comprise salts of Nitrite such as sodium nitrite, potassium nitrite, barium nitrite, calcium nitrite, and the like. For the exemplary purposes of this disclosure, Nitrite may comprise mixed salts of Nitrite such as nitrite orotate, and the like. Additionally, for the exemplary purposes of this disclosure, Nitrite may comprise nitrite esters such as amyl nitrite, and the like.

As used herein, "pharmaceutically acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

As used in this document, "pharmaceutically effective" is a phrase used in its broadest sense, including, by non-limiting example, effective in a clinical trial, for a specific patient, or only placebo-effective.

As used in this document, "Pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

Compounds/Components

A first implementation is a Carnitine compound of the formula:

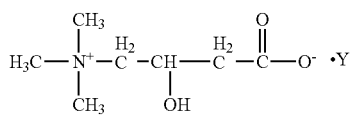

wherein;
Y is selected from the group consisting of a Nitrate and a Nitrite.

Applicants have cost-effectively synthesized Carnitine Nitrate by combining nitric acid and Carnitine, mixing with water, and leaving to crystallize. Further nitratization can take place, yielding Carnitine Dinitrate or Carnitine Trinitrate. An alternative implementation may comprise using Nitrous Acid ($HNO_2$) instead of Nitric Acid ($HNO_3$), thus yielding Carnitine Nitrite. Carnitine Nitrite has the same effects as Carnitine Nitrate, the only difference being that it requires one less step to yield Nitric Oxide (NO—). Mixed salts may also be used, such as in the non-limiting example of Carnitine Nitrate-Orotate. In addition, it will be understood that alternative implementations comprising Acetyl-L-Carnitine and/or Propionyl-L-carnitine in combination with one of a Nitrate and a Nitrite are likewise possible in accordance with these disclosures.

Another implementation is a Taurine compound of the formula:

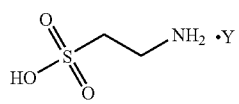

wherein;
Y is selected from the group consisting of a Nitrate and a Nitrite.

Applicants have cost-effectively synthesized Taurine Nitrate by combining nitric acid and Taurine, mixing with water, and leaving to crystallize. Further nitratization can take place, yielding Taurine Dinitrate or Taurine Trinitrate. An alternative implementation may comprise using Nitrous Acid ($HNO_2$) instead of Nitric Acid ($HNO_3$), thus yielding Taurine Nitrite. Taurine Nitrite has the same effects as Taurine Nitrate, the only difference being that it requires one less step to yield Nitric Oxide (NO—). Mixed salts may also be used, such as in the non-limiting example of Taurine Nitrate-Orotate.

Compositions and/or formulations of the present invention may be administered in any form, including one of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof for example. Compositions and/or formulations of the present invention may also include a acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

Implementations of Carnitine and Taurine Nitrate and/or Nitrite Compounds may also be synthesized or created in a wide variety of manners, and may be made from a wide variety of materials. Those of ordinary skill in the art will readily be able to select appropriate materials and methods to manufacture and use the compounds disclosed herein.

Dosage Forms

Implementations of Carnitine and Taurine Compounds may conveniently be presented in unit dosage form. Unit dosage formulations may be those containing a daily dose or unit, a daily sub-dose, or an appropriate fraction thereof, of the administered components as described herein.

A dosage unit may include a Carnitine and/or a Taurine Compound. In addition, a dosage unit may include a Carnitine and Taurine Compound admixed with a pharmaceutically acceptable additive(s), and/or any combination thereof.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

Manufacture

Implementations of Carnitine and Taurine Compounds may be made using conventional or other procedures. Accordingly, although there are a variety of method implementations for producing pharmaceutical compositions, for the exemplary purposes of this disclosure, a method implementation for producing a Carnitine and Taurine Compounds may comprise: measuring specific quantities of Carnitine and/or Taurine, Nitric or Nitrous Acid and water mixed in a specific order the measured quantities of Carnitine and/or Taurine, Nitric or Nitrous Acid and water, and any additional pharmaceutically acceptable additives or inert ingredients, and then separating the pharmaceutical composition into discrete quantities for distribution and/or administration.

Measuring specific quantities of Carnitine and/or Taurine, Nitric or Nitrous Acid and water, and pharmaceutically acceptable additives or inert ingredients, may involve any number of steps and implementing components, and measuring specific quantities of Carnitine and/or Taurine, Nitric or Nitrous Acid and water, and pharmaceutically acceptable additives or inert ingredients, may be accomplished readily from this disclosure. For the exemplary purposes of this disclosure, measuring specific quantities of Carnitine and/or Taurine, Nitric or Nitrous Acid and water, and pharmaceutically acceptable additives or inert ingredients, may comprise using a scale, a solid or liquid dispensing apparatus, or other measurement device capable of measuring solid mass or liquid volume to produce a desired quantity of Carnitine and/or Taurine, Nitric or Nitrous Acid and water, and pharmaceutically acceptable ingredient.

It should be appreciated that any of the components of particular implementations of Carnitine and Taurine Compounds may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion Compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of Carnitine and/or Taurine, Nitric or Nitrous Acid and water, and pharmaceutically acceptable additives or inert ingredients, may involve any number of steps and implementing components, and may be accomplished readily from this disclosure. For the exemplary purposes of this disclosure, mixed the measured quantities of Carnitine and/or Taurine, Nitric or Nitrous Acid and water, and pharmaceutically acceptable additives or inert ingredients, may comprise combining the measured quantities of Carnitine and/or Taurine, Nitric or Nitrous Acid and water, and pharmaceutically acceptable additives or inert ingredients, under the influence of physical, ultrasonic, or electrostatic forces to create a desired degree of intermingling and/or chemical reaction of the Carnitine and/or Taurine, Nitric or Nitrous Acid and water and any pharmaceutically acceptable ingredients. The mixed may be accomplished when the Carnitine and/or Taurine, Nitric or Nitrous Acid and water and/or any pharmaceutically acceptable ingredients are in a solid, liquid, or semisolid state.

Separating Carnitine and Taurine Compounds into discrete quantities for distribution may involve any number of steps and implementing components, and separating t Carnitine and Taurine Compounds into discrete quantities for distribution may be accomplished readily from this disclosure. For the exemplary purposes of this disclosure, separating the Amino Acid Compound into discrete quantities for distribution may involve utilizing a specific piece of equipment, for example, a conventional tablet forming apparatus to shape the formed composition into individual tablets, each containing a desired dose of Carnitine and Taurine Compounds. The separating process may be accomplished when the Carnitine and Taurine Compounds are in a solid, liquid, or semisolid state.

Those of ordinary skill in the art will be able to readily select manufacturing equipment and pharmaceutically acceptable additives or inert ingredients to manufacture implementations of Carnitine and Taurine Compounds. For the exemplary purposes of this disclosure, some examples of pharmaceutically acceptable additives or inert ingredients and manufacturing process are included below, particularly those that relate to manufacture of implementations of Carnitine and Taurine Compounds in tablet form. Notwithstanding the specific examples given, it will be understood that those of ordinary skill in the art will readily appreciate how to manufacture implementations of Carnitine and Taurine Compounds according to the other methods of administration and delivery disclosed in this document.

A particular implementation of Carnitine and Taurine Compounds may include a lubricant. Lubricants are any antisticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of Carnitine and Taurine Compounds may also include a binder. Binders are any agents used to impart cohesive qualities to powdered material through particle-particle bonding. Binders may include, for example, matrix binders (e.g. dry starch, dry sugars), film binders (e.g. celluloses, bentonite, sucrose), and chemical binders (e.g. polymeric cellulose derivatives, such as methyl cellulose, carboxy methyl cellulose, and hydroxy propyl cellulose); and other sugar, gelatin, non-cellulosic binders and the like.

Disintegrators may be used in particular implementations of Carnitine and Taurine Compounds to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Implementations of Carnitine and Taurine Compounds may include diluents, or any inert substances added to increase the bulk of the Carnitine and Taurine Compounds to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may be included in Carnitine and Taurine Compounds and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

Implementations of Carnitine and Taurine Compounds may also be administered through use of amphipathic lipid delivery systems (such as liposomes and unilamellar vesicles), caplet systems, oral liquid systems, parenteral and/or intravenous systems, topical systems (creams, gels, transdermal patches, etc.), intranasal systems, rectal or vaginal systems, and many other delivery methods and/or systems known to those of ordinary skill in the art. Those of ordinary skill in the art will readily be able to select additional pharmaceutically acceptable additives to enable delivery of implementations of a pharmaceutical composition from the disclosure in this document.

With respect to delivery of particular implementations of Carnitine and Taurine Compounds, for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, rectangular or triangular, for example. The tablets may be optionally scored so that they may be separated into different dosages. They may differ greatly in size and weight depending on the amount of the pharmaceutically acceptable active agent or agents present and the intended route of administration. They are divided into two general classes, (1) compressed tablets, and (2) molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi-particulate composition, a coated multiparticulate composition, an ion-exchange resin-based composition, an osmosis-based composition, or a biodegradable polymeric composition.

While manufacture of implementations of Carnitine and Taurine Compounds have been described in particular sequences of steps and/or in particular forms, it will be understood that such manufacture is not limited to the specific order of steps or forms as disclosed. Any steps or sequences of steps of manufacture of implementations of Carnitine and Taurine Compounds in any form are given as examples of possible steps or sequences of steps or potential forms and not as limitations, since many possible manufacturing processes and sequences of steps may be used to manufacture Carnitine and Taurine Compound implementations in a wide variety of forms.

Use

Implementations of Carnitine and Taurine Compounds are particularly useful in increasing vasodilation and blood flow in humans and animals. However, implementations are not limited to uses relating to vasodilation modification, and the like. Rather, any description relating to the foregoing is for the exemplary purposes of this disclosure. It will be understood that implementations of Carnitine and Taurine Compounds may encompass a variety of uses and are not limited in their uses. For example, possible uses may be, by non-limiting example, improved athletic performance, increased distribution to muscles, faster action than single-administration Carnitine and/or Taurine, enhanced water solubility, prevention of Nitrate tolerance, and/or countering Nitric Oxide inhibiting effects of certain Amino Acids.

In conventional preparations of Nitrate compounds, "tolerance," a particular side effect, has been observed in many patients. This is unfortunate because the effectiveness of Nitrate on vasodilation is well documented. "Tolerance" occurs when a subject's reaction to Nitrate decreases so that larger doses are required to achieve the same effect. A Mar. 3, 2000 report in the British Journal of Pharmacology indicates that "tolerance to the dilator effects of nitrates remains a persisting therapeutic problem." Raymond J. MacAllister "Arginine and Nitrate Tolerance" available at http://www.nature.com/bjp/journal/v130/n2/full/0703340a.html, the contents of which are hereby incorporated herein by reference.

Empirical studies indicate that Nitrates are useful for their vasolidating effects. Common Nitrates include nitroglycerin and isosorbide dinitrate. Nitrates exert their vasodilating effect through their reduction to Nitrites. In vivo, Nitrates are reduced to Nitrites and, in the blood vessels' epithelial cells, Nitrite reacts with a thiol donor (mainly glutathione) to yield Nitric Oxide. Louis J. Ignarro, "After 130 years, the Molecular Mechanism of Action of Nitroglycerin is Revealed" (Jun. 11, 2002) available at http://www.pnas.org/cgi/content/full/99/12/7816?ck=nck, the contents of which are hereby incorporated herein by reference.

The Nitric Oxide inhibiting characteristics of the Amino Acid Glutamine have been well documented in a number of studies. In particular, a Mar. 28, 2006 report in the American Journal of Physiology has found that Glutamine inhibits Nitric Oxide production by downregulation of eNOS synthase. Masao Kakoki, et al. "Amino acids as Modulators of Endothelium-Derived Nitric Oxide." available at http://ajprenal.physiology.org/cgi/content/full/291/2/F297, the contents of which are hereby incorporated by reference.

A January 2006 *Journal of Nutrition* report indicates that the Amino Acid Leucine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the Amino Acid Norvaline inhibits the enzyme arginase and thus decreases the rate of conversion of the Amino Acid Arginine to urea. Takeyori Saheki, et al. "Regulation of Urea Synthesis in Rat Liver" available at http://jb.oxfordjournals.org/cgi/content/abstract/86/3/745?ijkey=5d134456b7443ca36c809269462276e532549798& keytype2=tf_ipsecsha, the contents of which are hereby incorporated by reference.

An October 2004 *Journal of Nutrition* report indicates that the Amino Acid Ornithine promotes anabolism and stimulates muscle protein synthesis. Michael J. Rennie, et al. "Branched-Chain Amino Acids as Fuels and Anabolic Signals in Human Muscle" available at http://jn.nutrition.org/cgi/content/full/136/1/264S, the contents of which are hereby incorporated by reference.

Empirical studies indicate that the Amino Acids Beta-Beta Alanine and L-Histidine support carnosine production. M. Dunnett, "Influence of Oral Beta-Beta Alanine and L-Histidine Supplementation on the Carnosine Content of the Gluteus Medius" Equine Veterinary Journal Supplement, availableathttp://www.ncbi.nlm.nih.gov/sites/entrez?Db=pubmed&Cmd=ShowDetailView&Term ToSearch=10659307&ordinalpos=4&itool=EntrezSystem2.PEntrez.Pubmed.Pubmed, the contents of which are hereby incorporated by reference.

Empirical studies further indicate that the Amino Acids Beta Alanine and L-Histidine increase muscle power, recuperation and stamina.ii Yoshihiro Suzuki "High Level of Skeletal Muscle Carnosine Contributes to the Latter Half of Exercise Performance During 30-S Maximal Cycle Ergometer Sprinting" in the Japanese Journal of Physiology, available at http://www.ncbi.nlm.nih.gov/sites/entrez?Db=pubmed&Cmd=ShowDetailView&TermToSearch=12139778&ordinalpos=4&itool=EntrezSystem2.PEntrez.Pubmed.Pubmed_ResultsPanel.Pubmed_RVDocSum, the contents of which are hereby incorporated by reference.

Accordingly, Applicants have discovered that the Carnitine compound according to the first implementation, when ingested, provides enhanced Nitric Oxide (NO—) production while providing improved vasodilation effects over single administration of Carnitine, the single administration of Nitrates, or the single administration of Nitrites. Improved vasodilation may, in turn, provide better circulation and distribution of Carnitine in the body. Absorption may be improved since Amino Acid derivative salts with inorganic acids may be much more water soluble than single administration Amino Acid derivatives. Applicants have also discovered that the vasodilating effect of Carnitine Nitrate and Taurine Nitrate manifests as fast as any nitrate, since the $NO_3$— group of the salt requires minimal conversion to yield Nitric Oxide. Likewise, the development of tolerance to the nitrate component of the molecule may be prevented with the presence of Carnitine and/or Taurine.

What is claimed is:

1. A Carnitine Compound consisting essentially of a nitrate or nitrite of Carnitine.

2. A Taurine Compound consisting essentially of a nitrate or nitrite of Taurine.

3. A method for increasing water solubility of one of Carnitine and Taurine in a human or animal, which comprises administering a pharmaceutically effective amount of one of a Carnitine Compound consisting essentially of a nitrate or nitrite of Carnitine and a Taurine Compound consisting essentially of a nitrate or nitrite of Taurine to the human or animal.

4. The method of claim 3, wherein increasing water solubility further comprises increasing the bioabsorption of one of Carnitine and Taurine in a human or animal.

5. The method of claim 3, wherein increasing water solubility further comprises increasing the vasodilative characteristics of one of Carnitine and Taurine in a human or animal.

6. A method for treating the development of nitrate tolerances in a human or animal, which comprises administering a pharmaceutically effective amount of one of a Carnitine Compound consisting essentially of a nitrate or nitrite of Carnitine and a Taurine Compound consisting essentially of a nitrate or nitrite of Taurine to the human or animal.

* * * * *